United States Patent
Manhard

(10) Patent No.: US 7,320,322 B2
(45) Date of Patent: Jan. 22, 2008

(54) VALVE FOR CONDUCTING HYPERPOLARIZED GAS

(75) Inventor: John Manhard, Durham, NC (US)

(73) Assignee: Medi-Physics, Inc., Princeton, NJ (US)

( * ) Notice: Subject to any disclaimer, the term of this patent is extended or adjusted under 35 U.S.C. 154(b) by 798 days.

(21) Appl. No.: 10/829,001

(22) Filed: Apr. 21, 2004

(65) Prior Publication Data

US 2005/0022814 A1 Feb. 3, 2005

(51) Int. Cl.
*A62B 9/02* (2006.01)
(52) U.S. Cl. .............................. 128/205.24; 128/204.18
(58) Field of Classification Search ........... 128/205.24, 128/202.27, 200.24, 204.18, 204.26, 204.27; 137/505.28, 507; 251/368
See application file for complete search history.

(56) References Cited

U.S. PATENT DOCUMENTS

| | | | | |
|---|---|---|---|---|
| 3,351,089 | A | * | 11/1967 | Garrahan .............. 137/599.04 |
| 5,549,134 | A | | 8/1996 | Browne et al. |
| 6,647,982 | B1 | * | 11/2003 | Zaiser et al. ........... 128/204.18 |
| 6,834,648 | B2 | * | 12/2004 | Tokasz et al. .......... 128/205.24 |

FOREIGN PATENT DOCUMENTS

| | | |
|---|---|---|
| DE | 10062792 | 7/2002 |
| WO | 02/04852 | 1/2002 |

OTHER PUBLICATIONS

International Search Report for PCT/US2004/012479 dated Aug. 30, 2004.

* cited by examiner

*Primary Examiner*—Steven O. Douglas
(74) *Attorney, Agent, or Firm*—Robert F. Chisholm

(57) ABSTRACT

The valve of the present invention provides a one-piece valve stem piston having a piston head and a piston stem. The piston head has a larger diameter than the piston stem. The stem incorporates only a single sliding O-ring in the area that seals the gas in the valve cylinder bore. The valve blocks gas flow by sealing against the positioning each O-ring over the gas flow port. This provides the valve with a low sliding friction upon piston movement. Pilot control air pressure is reduced because of the lower friction and due to the air operating on the larger surface area of the piston head. All materials in the construction of the valve are non-metallic.

9 Claims, 3 Drawing Sheets

VALVE FOR CONDUCTING HYPERPOLARIZED GAS

FIELD OF THE INVENTION

The present invention relates to devices for conducting and transferring hyperpolarized gases. More specifically, the present invention is directed to a valve used in a ventilator for alternately conducting hyperpolarized gas, oxygenated air, and vented exhaust air.

BACKGROUND OF THE INVENTION

There is a need for a pneumatic gas delivery valve that operates on lower control pressures than a spool valve and eliminates the problem of spool sticking. The valve needs to control two types of inhalation gases and to control the exhalation of the animal through a vent port. Additionally, the valve should be non-metallic and non-magnetic.

SUMMARY OF THE INVENTION

The valve of the present invention provides a one-piece valve stem piston having a piston head and a piston stem. The piston head has a larger diameter than the piston stem. The stem incorporates only a single sliding O-ring in the area that seals the gas in the valve cylinder bore. The valve blocks gas flow by sealing against the positioning each O-ring over the gas flow port. This provides the valve with a low sliding friction upon piston movement. Pilot control air pressure is reduced because of the lower friction and due to the air operating on the larger surface area of the piston head. All materials in the construction of the valve are non-metallic.

More particularly, the present invention provides a valve assembly for conducting hyperpolarized gas. The valve includes a valve cover and a valve body. The valve cover defines first, second, and third cover control gas ports. The valve body defines first, second, and third stepped piston bores opening on one major surface of the valve body. Each stepped piston bore defines a stem bore portion and a head bore portion. The valve body further defines first, second, and third body gas control ports in fluid communication with the head bore portion of the first, second, and third stepped piston bores, respectively. The valve body also defines first, second, and third breathing air ports in fluid communication with the stem bore portion of the first, second, and third stepped piston bores, respectively. The valve body further defines an elongate fluid passageway opening on the valve body and extending in fluid communication with the stem bore portion of the first, second, and third stepped piston bores. The valve assembly includes a first, second, and third piston slideably supported in a respective one of the first, second, and third stepped piston bores, respectively. Each piston includes a piston head received in the head bore portion of one of the stepped piston bores so that the piston head seals each cover control gas port from its corresponding body control gas port. Each piston also includes an elongate piston stem received in the stem bore portion of a respective stepped piston bore so that the piston stem seals its respective body control gas port from its corresponding breathing air port.

DETAILED DESCRIPTION OF THE PREFERRED EMBODIMENT

Figure 1:
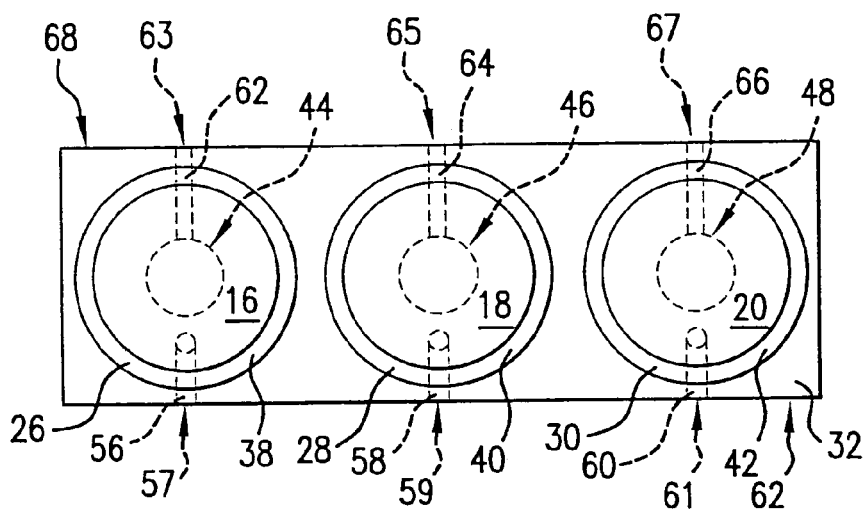
FIG. 1 depicts a valve assembly of the present invention with the valve cover removed.
Figure 2:
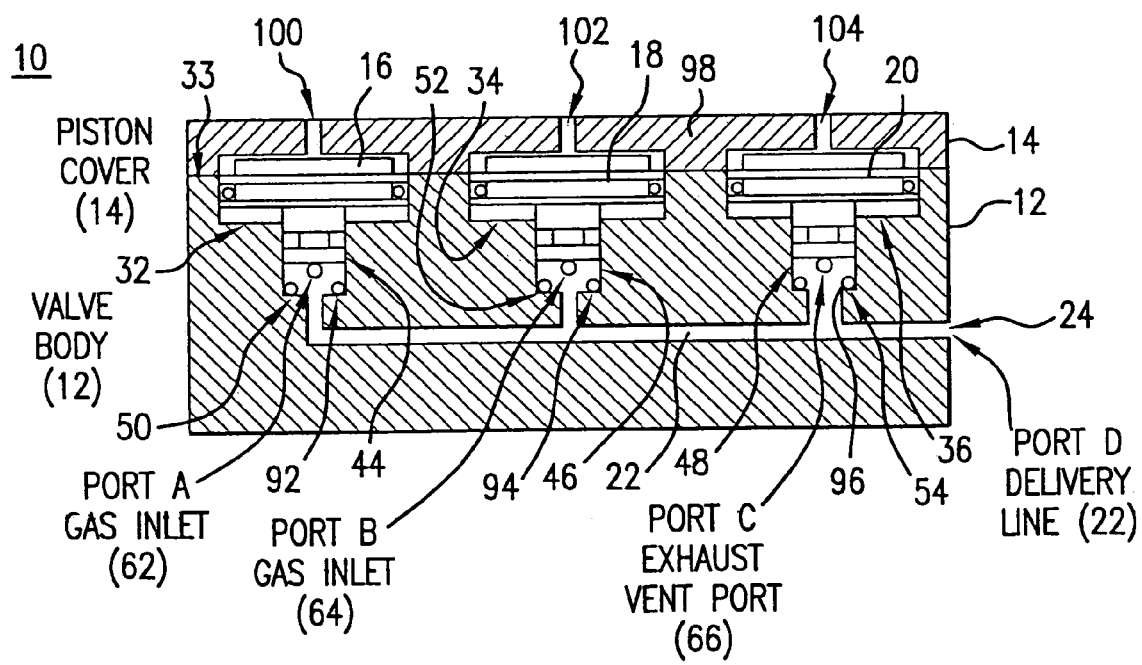
FIG. 2 is a cross-sectional view of a valve assembly of the present invention taken through line 2-2 of FIG. 7.
Figure 3:
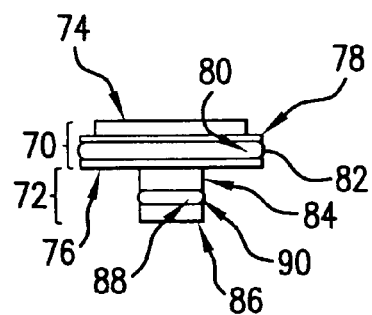
FIG. 3 is a side elevational view of a valve stem of the present invention.
Figure 4:
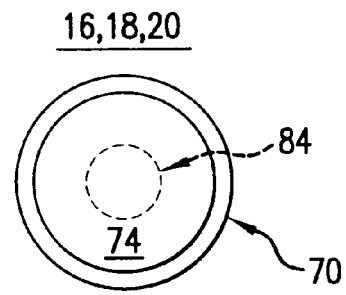
FIG. 4 is a top view of the valve stem of FIG. 3.
Figure 5:
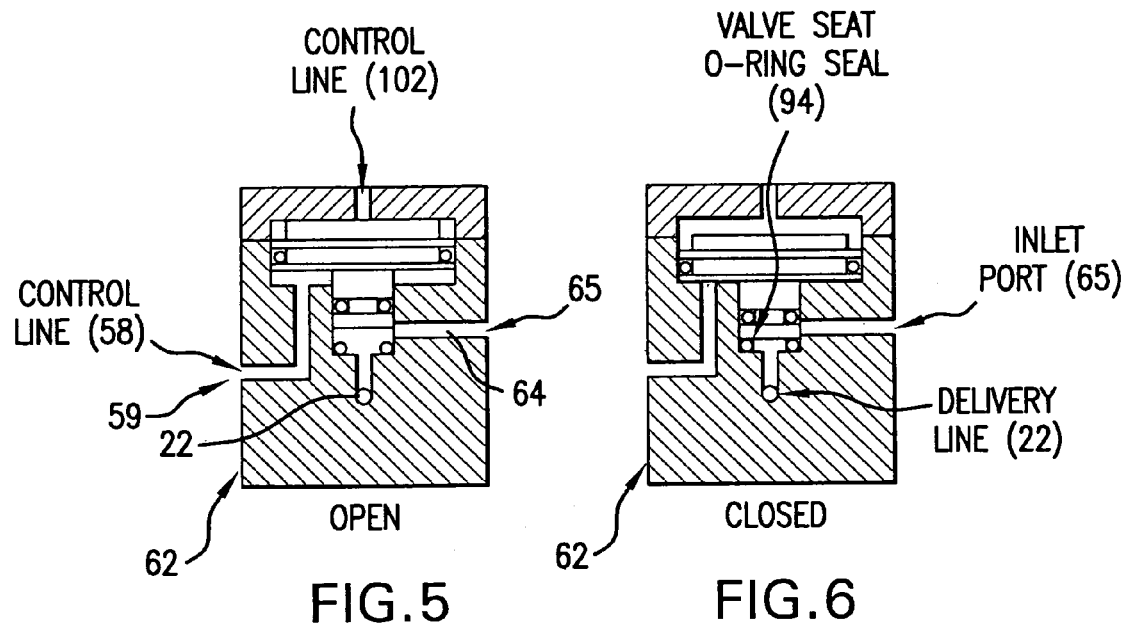
FIG. 5 is a cross-sectional view of the valve assembly of FIG. 7 taken through the line 5-5 showing a piston in a position to allow flow of a gas past the valve seat.
Figure 6:
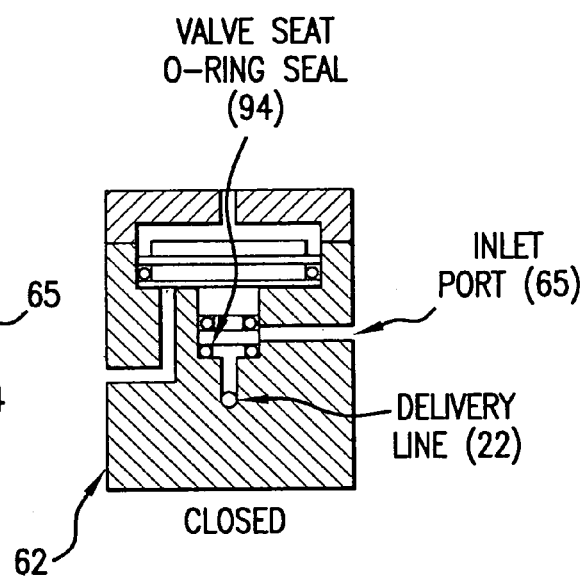
FIG. 6 is the cross-sectional view of FIG. 5 showing the piston in a position to block flow of a gas past the valve seat.
Figure 7:
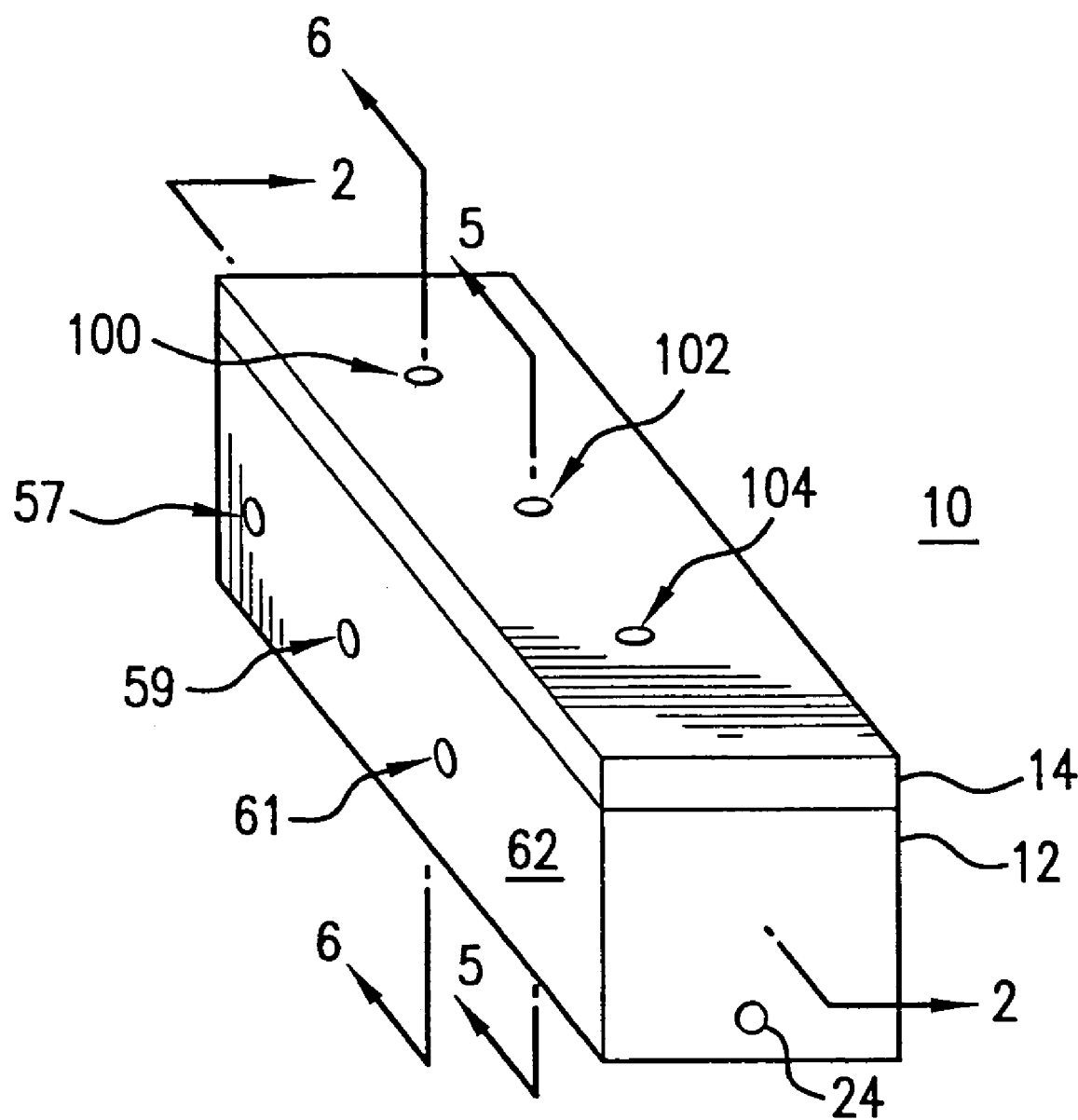
FIG. 7 depicts a valve assembly of a valve assembly of the present invention.

Referring to FIGS. 1-7, the present invention provides a valve assembly 10.

Valve 10 is an assembly of a valve body 12 and valve cover 14 which supports first, second and third valve pistons 16, 18, and 20, respectively. Valve body 12, valve cover 14, and any fittings connected thereto are desirably formed from a thermoplastic material so as to minimize the deleterious effect on a hyperpolarized noble gas passing therethrough. Valve 10 is desirably used with a ventilator for controlling the delivery of breathing gases therethrough. Valve 10 is able to selectively deliver breathing air and a hyperpolarized gas to a subject for inhalation and to vent exhaled air from the subject.

Valve body 12 defines an elongate gas delivery passageway 22 opening on valve body 12 at port 24. Valve body 12 further defines a first, second, and third stepped piston bore 26, 28, and 30 opening on major surface 33. Stepped piston bores 26, 28, and 30 receive therein first, second, and third pistons 16, 18, and 20, respectively. For each stepped piston bore 26, 28, and 30, valve body 12 includes a first inwardly-extending annular rim 32, 34, and 36, and a cylindrical interior wall 38, 40, and 42 extending therefrom to major surface 33. Valve body 12 further includes a second cylindrical interior wall 44, 46, and 48 extending from first annular rim 32, 34, and 36 to a second inwardly-extending annular rim 50, 52, and 54, respectively.

Valve body 12 further defines first, second, and third control air passages 56, 58, and 60 opening on exterior surface 62 at ports 57, 59, and 61 and on first annular rim 32, 34, and 36, respectively. Similarly, valve body 12 defines first, second, and third breathing gas passageways 62, 64, and 66 opening on exterior surface 68 at ports 63, 65, and 67 and on second cylindrical interior wall 44, 46, and 48, respectively.

Each valve piston 16, 18, and 20 includes a piston head 70 and a piston stem 72. Piston head 70 includes opposing major surfaces 74 and 76 and a cylindrical head wall 78 extending therebetween. Head wall 78 desirably defines an annular groove 80 supporting an elastomeric O-ring 82 therein. O-ring 82 slideably engages first interior wall 38, 40, or 42, as appropriate. Piston stem 72 includes an elongate cylindrical wall 84 extending to free end 86. Wall 84 defines an annular groove 88 supporting elastomeric O-ring 90 for slideable sealing engagement against second interior wall 44, 46, or 48, as appropriate. O-ring 90 is supported at a location so as to seal the breathing gases in passageways 62, 64, and 66 from control air within passageways 56, 58, and 60, respectively, at all times.

Valve 10 supports O-rings 92, 94, and 96 upon second annular rim 50, 52, and 54 for seating free ends 86 of each respective piston thereagainst.

Valve cover 14 includes an elongate planar body 98 defining a first, second, and third cover control air passageways 100, 102, and 104 therethrough so as to be in overlying spaced registry with the first major surface 74 of pistons 16, 18, and 20, respectively. Valve cover 14 is desirably affixed to valve body 12 by a non-metallic adhesive such as a cyanoacrylate.

In operation, the flow of breathing gases through passageways 62, 64, and 66 into gas delivery passageway 22 by the position of each piston 16, 18, and 20, respectively. The position of each piston is controlled by the delivery of competing air pressures acting either on second major surfaces 76 through body passages 56, 58, and 60 or on first major surfaces 74 through cover passageways 100, 102, and 104.

For example, a ventilator system may connect a source for normal breathing air to port 63, hyperpolarized gas to port 65, and use port 67 as an exhaust vent. Delivery passageway 22 is connected in fluid communication with the tracheal tube of an animal under test. During the inhalation cycle, pistons 16 and 18 are raised so as to unblock flow through passageways 62 and 64 and lowers piston 20 so as to block flow out port 67 through vent passageway 66. Alternatively, boluses of breathing air and hyperpolarized gas may be individually delivered to the subject by selectively lowering either piston 16 or 18 while piston 20 is also lowered. During the exhalation cycle, pistons 16 and 18 are lowered so as to prevent flow into or from passageway 22 and piston 20 is raised so as to allow exhaled gas to be vented through exhaust port 67. Additionally, each piston 16, 18, and 20 may be lowered to block all flow through passageways 62, 64, and 66 during the exhalation cycle so as to cause the animal to hold its breath for MRI lung imaging.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A valve assembly for conducting hyperpolarized gas, comprising:

a valve cover defining first, second, and third cover control gas ports;

a valve body defining first, second, and third stepped piston bores opening on one major surface of said valve body, each said stepped piston bore defining a stem bore portion and a head bore portion;

first, second, and third body gas control ports in fluid communication with the head bore portion of said first, second, and third stepped piston bores, respectively, first, second, and third air breathing ports in fluid communication with the stem bore portion of said first, second, and third stepped piston bores, respectively, and an elongate fluid passageway opening on said valve body and in fluid communication with the stem bore portion of said first, second, and third stepped piston bores; and a first, second, and third piston slideably supported in said first, second, and third stepped piston bore, respectively, each said piston including a piston head received in the head bore portion of one of said first, second, and third stepped piston bores, said piston head sealing each said cover control gas port from its corresponding said body control gas port; and an elongate piston stem received in the stem bore portion of said one of said stepped piston bores, said piston stem sealing each said body control gas port from its corresponding said breathing air port.

2. The valve assembly of claim 1, wherein at least one of said valve cover and valve body are formed from a thermoplastic material.

3. The valve assembly of claim 1, wherein said valve cover and valve body are formed from a thermoplastic material.

4. The valve assembly of claim 1, wherein said first air breathing port is in fluid communication with a source of breathing air, said second air breathing port is in fluid communication with a source of hyperpolarized gas, and said third air breathing port is in fluid communication with a vent to atmosphere.

5. The valve assembly of claim 1, wherein said first and second pistons are urged towards said cover so as to allow a hyperpolarized gas mixture to be inhaled by a subject.

6. The valve assembly of claim 5, wherein said third piston is urged away from said cover so as prevent exhaling by said subject.

7. The valve assembly of claim 1, wherein said first and second pistons are urged away from said cover so as to prevent a hyperpolarized gas mixture from being administered to a subject.

8. The valve assembly of claim 7, wherein said third piston is urged towards said cover so as to allow said subject to exhale.

9. The valve assembly of claim 1, further comprising a first gasket about each said piston head, a second gasket about each said piston stem, and a third gasket seated in each said stem bore portion, said first and second gaskets being slideable within said valve body and said third gaskets being stationary so as to be compressed by its respective piston stem when urged away from said valve cover and thereby fluidly isolating its respective air breathing port from said fluid passageway.

* * * * *